United States Patent

Averkiou et al.

(10) Patent No.: US 6,186,950 B1
(45) Date of Patent: Feb. 13, 2001

(54) ULTRASONIC PULSE INVERSION HARMONIC SEPARATION WITH REDUCED MOTIONAL EFFECTS

(75) Inventors: Michalakis Averkiou, Kirkland; Jeffry E. Powers, Bainbridge Is., both of WA (US)

(73) Assignee: ATL Ultrasound, Bothell, WA (US)

( * ) Notice: Under 35 U.S.C. 154(b), the term of this patent shall be extended for 0 days.

(21) Appl. No.: 09/434,328

(22) Filed: Nov. 4, 1999

(51) Int. Cl.$^7$ .................................................. A61B 08/00
(52) U.S. Cl. ......................... 600/443; 600/447; 600/440
(58) Field of Search ................................. 600/437, 443, 600/440, 444, 447, 445; 128/916

(56) References Cited

U.S. PATENT DOCUMENTS

| 5,623,928 | 4/1997 | Wright et al. . |
| 5,706,819 | 1/1998 | Hwang et al. . |
| 5,833,613 | * 11/1998 | Averkiou et al. ................... 600/440 |
| 5,951,478 | 9/1999 | Hwang et al. . |
| 5,961,463 | * 10/1999 | Rhyne et al. ........................ 600/458 |

FOREIGN PATENT DOCUMENTS

WO 99/30617    6/1999   (WO) .

OTHER PUBLICATIONS

U.S. application No. 09/156,097, Burns et al., filed Sep. 17, 1998.
Simpson et al., "Pulse Inversion Doopler: A New Method for Detecting Nonlinear Echoes from Microbubble Contrast Agents." pp. 1–30, Mar. 31, 1998.

* cited by examiner

Primary Examiner—Marvin M. Lateef
Assistant Examiner—Maulin Patel
(74) Attorney, Agent, or Firm—W. Brinton Yorks, Jr.

(57) ABSTRACT

Pulse inversion harmonic separation is performed utilizing echoes from three or more pulses of alternating phase or polarity. Temporally different echoes of opposite phase or polarity are combined in pairs, which are in turn combined to form partial sums and a final sum in which fundamental frequency signal components are substantially eliminated. Preferably the signals are normalized to a common reference level. The inventive technique can be performed by a filter structure using weighting coefficients exhibiting a Gaussian variation.

30 Claims, 7 Drawing Sheets

To Beamformer

ULTRASONIC PULSE INVERSION HARMONIC SEPARATION WITH REDUCED MOTIONAL EFFECTS

This invention relates to ultrasonic diagnostic imaging systems which separate fundamental and harmonic frequency signals by the pulse inversion technique and, in particular, to the enhancement of such systems by reducing the effects of motion.

U.S. Pat. No. 5,706,819 and 5,951,478 describe a technique for separating the fundamental and harmonic frequency components of ultrasonic signals known as pulse inversion. As described in those patents, a target is insonified by two or more fundamental frequency pulses of different phase or polarity and echoes are received following each pulse. The received echoes will contain both fundamental and harmonic frequency components, due either to the presence of contrast agents in the body or the nonlinear response of tissue to the transmitted waves. When depth-corresponding received echoes of the two pulse transmissions are combined, the fundamental frequency components of the echo signals will cancel due to the linear nature of those components and the differing phase or polarity of the transmit pulses. The harmonic components however, being quadratically proportional to the incident pressure wave, will not cancel but will reinforce each other. As the patents indicate, when the target medium is stationary or quasi-stationary, almost complete cancellation of the fundamental components will occur, leaving separated harmonic components.

While the assumption of a stationary or quasi-stationary medium may be relatively valid for static tissue and organs, it is only an approximation for moving tissue such as the beating heart. For example, when myocardial perfusion is being assessed by pulse inversion harmonic techniques, the continually moving heart walls will introduce motional effects into the echoes received from the multiple transmit pulses. As a result, the fundamental components will only partially cancel and the residual fundamental components will constitute unwanted noise or artifacts in the desired harmonic signals. Hence it would be desirable to enhance the practice of the pulse inversion technique so that fundamental components would be virtually completely cancelled, even in the presence of these motional effects.

In accordance with the principles of the present invention, the pulse inversion technique is enhanced to reduce motional effects by insonifying a target with three or more transmit pulses of differing phase or polarity. Pairs of echoes from the target from oppositely phased or poled transmit pulses are combined to form partial echo sums, and the partial sums are accumulated to form a full echo sum comprising harmonic signals in which fundamental components are significantly reduced. In general, the use of a greater number of transmit pulses and echoes results in greater fundamental component reduction. In a preferred embodiment, a sequence of echoes from a target from phase- or polarity-alternating pulses is processed by a filter structure utilizing a continually varying sequence of weighting coefficients. The coefficients may exhibit a Gaussian variation and may conveniently be computed for any number of samples by using the rule of Pascal's triangle. Preferably the filter coefficients are scaled so that the separated harmonic signals are concurrently normalized in amplitude.

Figure 1A:
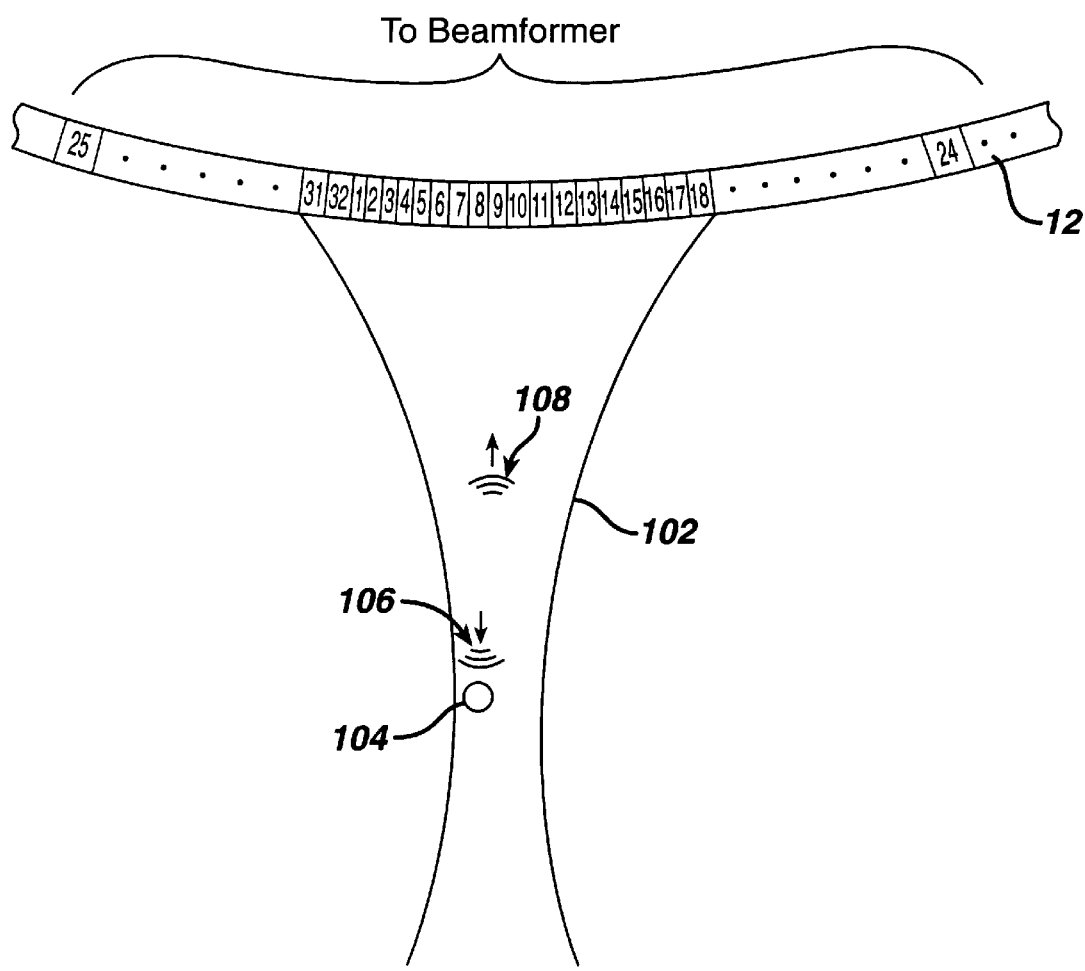
FIGS. 1a and 1b illustrate the operation of the pulse inversion technique when a target is stationary.

Referring first to FIG. 1a, an ultrasonic transducer array 12 is shown which is composed of a number of separate transducer elements. The elements of the array are excited in sequences known in the art to transmit steered and focused beams of ultrasonic energy. The profile of one such transmit beam 102 is shown in the drawing. Insonified by the transmit beam 102 in this example is a stationary object 104, such as a cyst or stationary contrast agent microbubble. The transmit pulse wavefront of the beam travels to the object 104 as indicated by the arrow and wave 106, and an echo is returned to the transducer array 12 from object 104 as indicated by the arrow and echo 108. The echo waves are received by the elements of the array and coupled to a beamformer, which delays and combines the echo signal components to produce a coherent echo signal.

Figure 1B:
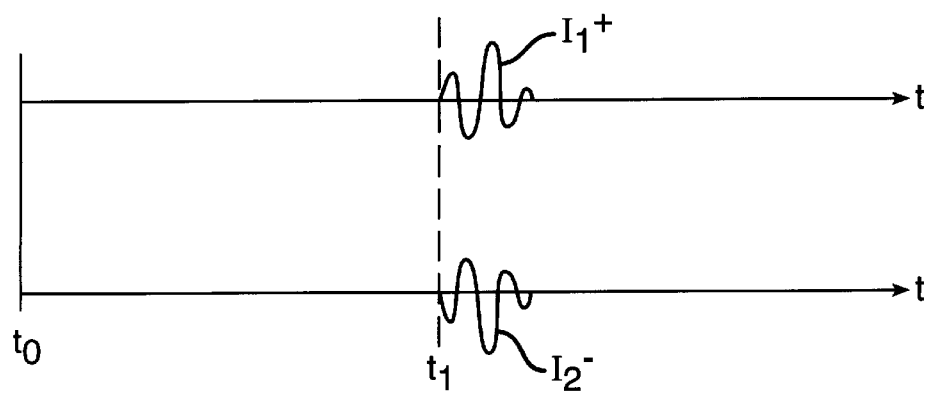

FIG. 1b illustrates the echoes returned from two interrogations of object 104 by the transmission of two beams with opposite polarity or phase. In this drawing the fundamental frequency characteristic of the echoes are represented as a result of the fundamental frequency characteristic of the transmit pulses. The first echo $I_1^+$ and the second echo $I_2^-$ are in phase opposition by virtue of the differing characteristics of the transmit pulses. Both echoes are drawn on time axes with a commonly referenced origin $t_0$, which is generally the time at which each transmit pulse is launched. Since the object 104 is stationary, each pulse is received at the same time reference point $t_1$, the $t_0$–$t_1$ time interval being the time required for the ultrasound pulse to travel to the object and for the echo to return to the transducer array. The $t_0$–$t_1$ time-of-flight interval is the basis for positionally locating the object 104 in the ultrasound image, but in pulse inversion the alignment of both echoes to the same $t_1$ time reference means that the two echoes can be combined to cancel each other by reason of their phase opposition. Thus the fundamental frequency components of the two echoes are eliminated by this cancellation and the harmonic components (not shown), which are not in phase opposition, will remain in the echoes. This is the basis of pulse inversion harmonic separation.

Figure 2A:
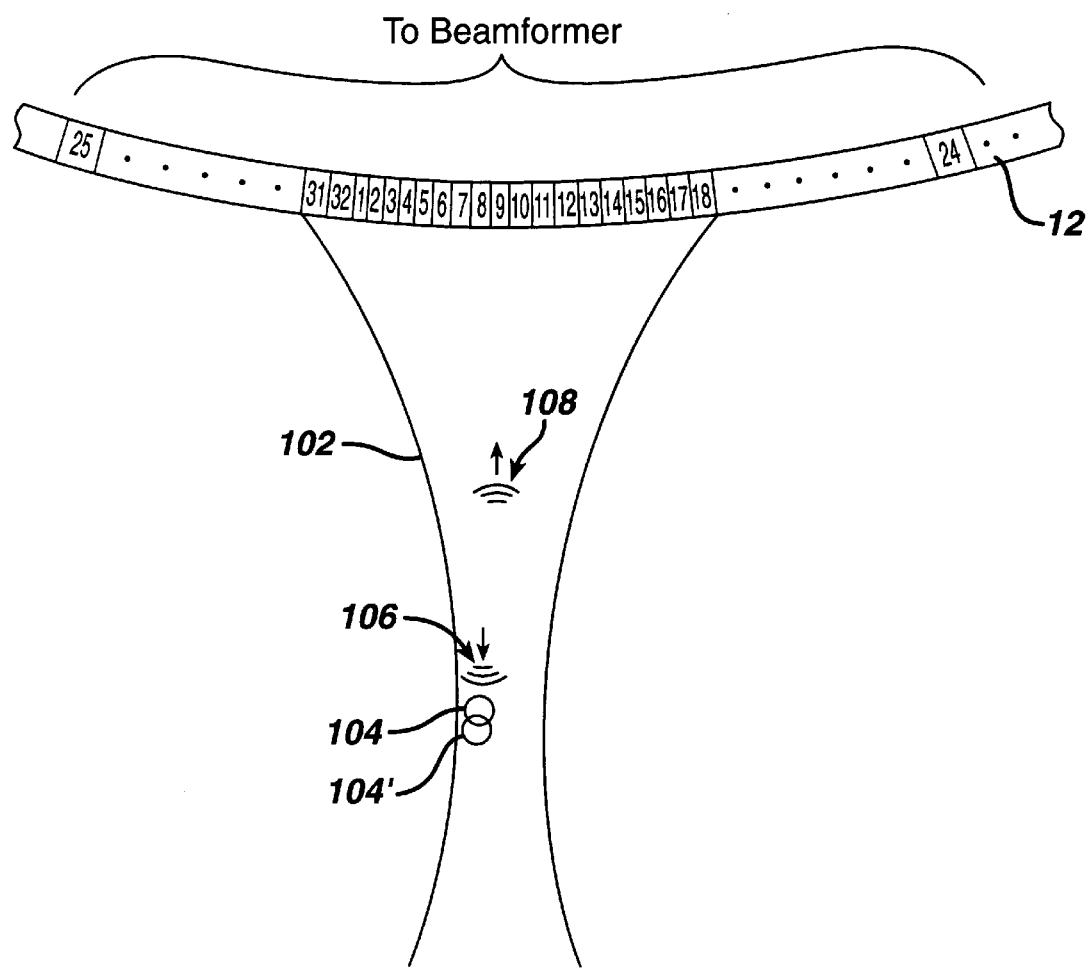
FIGS. 2a and 2b illustrate the operation of the pulse inversion technique when a target is moving.

FIG. 2a shows a second scenario, but in this case the object 104 is in motion. This would be the case of a microbubble in the vasculature of the myocardium, which would be continually moving since the myocardium is continually contracting and relaxing as the heart beats. Whereas the microbubble may be exhibiting little or no motion within the blood vessel, the vessel itself is moving by virtue of the pulsatile movement of the heart. In this example the object 104 is at the location shown at the time the first echo $I_1^-$ from the first transmit pulse is returned from the object. The object is at a different location 104' at the time the second echo $I_2^-$ is returned from the second transmit pulse. Since the object is at a different location 104, 104' each time it is interrogated by reason of the motion of the tissue containing the target object, the time-of-flight of the two echoes are different, as shown by the different time references $t_1$ and $t_2$ in FIG. 2b. Thus, the $t_1$–$t_2$ interval is caused by the movement of the object 104, 104' during the interpulse interval. It must be remembered that a pulse-echo ultrasound system is a stochastic process and does not continuously monitor motion as the ultrasound mode known as continuous wave Doppler does. Each interrogation of the image field is only a snapshot in time of the location of objects in the field at that exact moment of interrogation. When an object is at two different locations in two consecutive snapshots, it is probable that the object in both snapshots is the same object, and appears in different locations because it has moved during the interval between the snapshots. It is also possible that each snapshot is showing a distinctly different object, but when some empirical expectations are applied such as the nominal speed of the flow of blood, the nominal speed of tissue motion, and the spatial proximity of the echoes, this alternative may be probabilistically ruled out. Applying these empirical parameters, the greater probability is that the echoes returned from the same vicinity from two pulses transmitted in rapid succession within the same or substantially the same beam profile are from an object that is in motion.

Figure 2B:
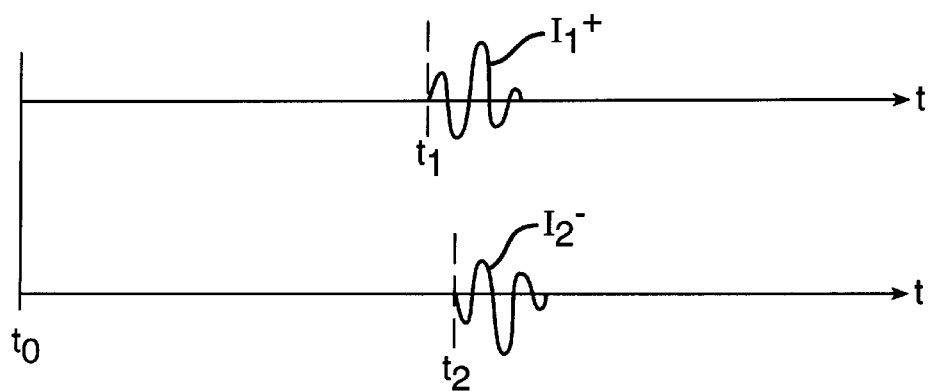

FIG. 2b illustrates the problem created for pulse inversion harmonic separation by reason of this motion. The two echoes $I_1^+$ and $I_2^-$ are offset in time by the $t_1$–$t_2$ interval and therefore are not aligned in phase opposition. When the two echoes are combined to cancel the illustrated fundamental components, the components will no longer completely cancel. In fact, the echoes from the differing transmit pulses may be phase shifted relative to each other such that the fundamental components additively combine and reinforce each other. The undesired phase shift disparity arises by reason of the need for two pulses, the motion of the target, and the time interval between pulses.

Figure 3A:
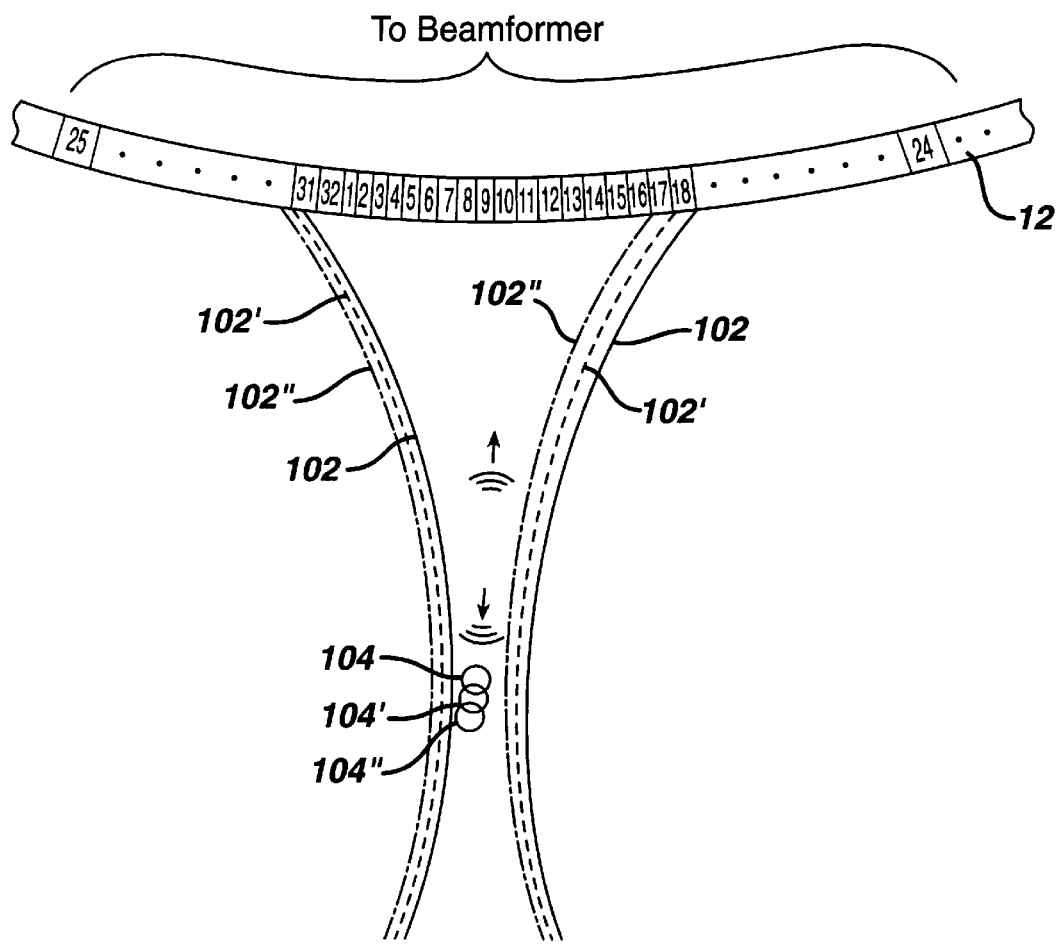
FIGS. 3a and 3b illustrate the operation of the pulse inversion technique with a moving target in accordance with the present invention.
Figure 3B:
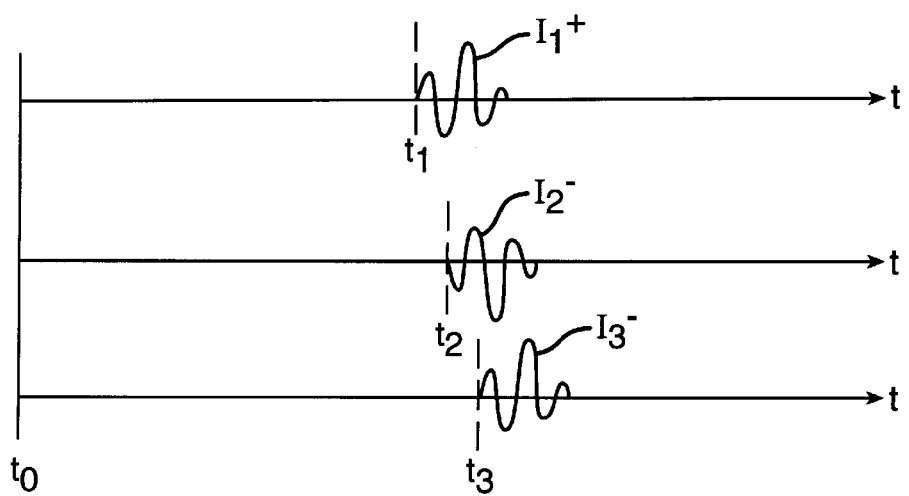

FIGS. 3a and 3b illustrate the solution to this motion problem in accordance with the present invention, which is to transmit at least one further pulse to receive at least one further echo. This solution is counterintuitive, since the problem is caused by the motion over the time interval between the transmit pulses; transmitting yet another pulse creates yet another interpulse time interval, and would intuitively seem to worsen the problem, not improve it. Continuing the example of FIG. 2a, FIG. 3a shows a moving object such as a microbubble in moving tissue which is at position 104 at the time it returns an echo $I_1^+$ from a first transmit pulse of a first phase or polarity. The moving object is at another position 104' when it returns an echo $I_2^-$ in response to a second transmit pulse of a second phase or polarity. The moving object is at a third position 104" at the time it returns an echo $I_3^+$ in response to a third transmit pulse having the same phase or polarity as the first pulse. The three resulting fundamental frequency echoes are shown in FIG. 3b. The second echo, resulting from a transmit pulse of a phase or polarity differing from that of the first and third echoes, is the inverse of the other two echoes. Each echo has a different time reference $t_1$, $t_2$, or $t_3$ to the time origin $t_0$ and to each other. Thus there are two interpulse intervals, the $t_1$–$t_2$ time interval and the $t_2$–$t_3$ time interval. While these time intervals may differ in length, it is preferred for reasons given below that they be of the same duration.

Figure 4:
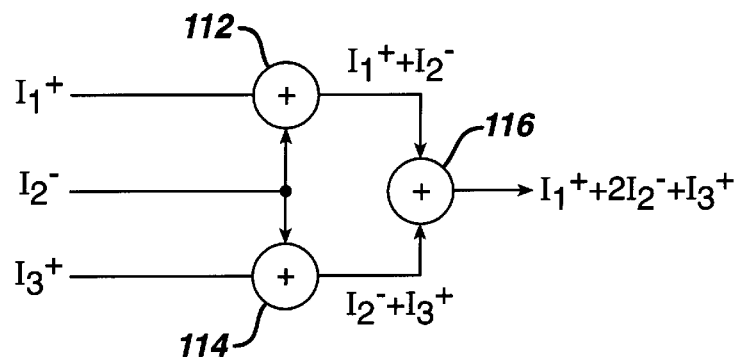
FIG. 4 illustrates a first embodiment of the present invention which performs pulse inversion harmonic separation with reduced motional effects.

FIG. 4 illustrates a processor which processes the echoes of FIG. 3b to produce separated harmonic signal components in which the incomplete fundamental cancellation effects of motion have been greatly reduced. The three echoes $I_1^+$, $I_2^-$, and $I_3^+$ are shown on the three lines at the left side of the drawing. In a constructed embodiment these three lines may comprise line stores which store the echo scanlines until they are to be processed. The first two echoes $I_1^+$ and $I_2^-$ which are of opposite polarity are summed in an adder 112 to form a first partial sum signal ($I_1^+$+$I_2^-$). This is recognized as the sum formed by conventional two-pulse pulse inversion to separate harmonic components. In accordance with the present invention, the second and third echoes $I_2^-$ and $I_3^+$ which are also of opposite polarity are summed in an adder 114 to form a second partial sum signal ($I_2^-$+$I_3^+$), also a convention two-pulse pulse inversion harmonic sum. The partial sum signals are then combined in an adder 116 to produce separated harmonic components in the form of ($I_1^+$+$2I_2^-$+$I_3^+$) in which the fundamental components are reduced even further than in either of the individual partial sum signals.

Figure 5:
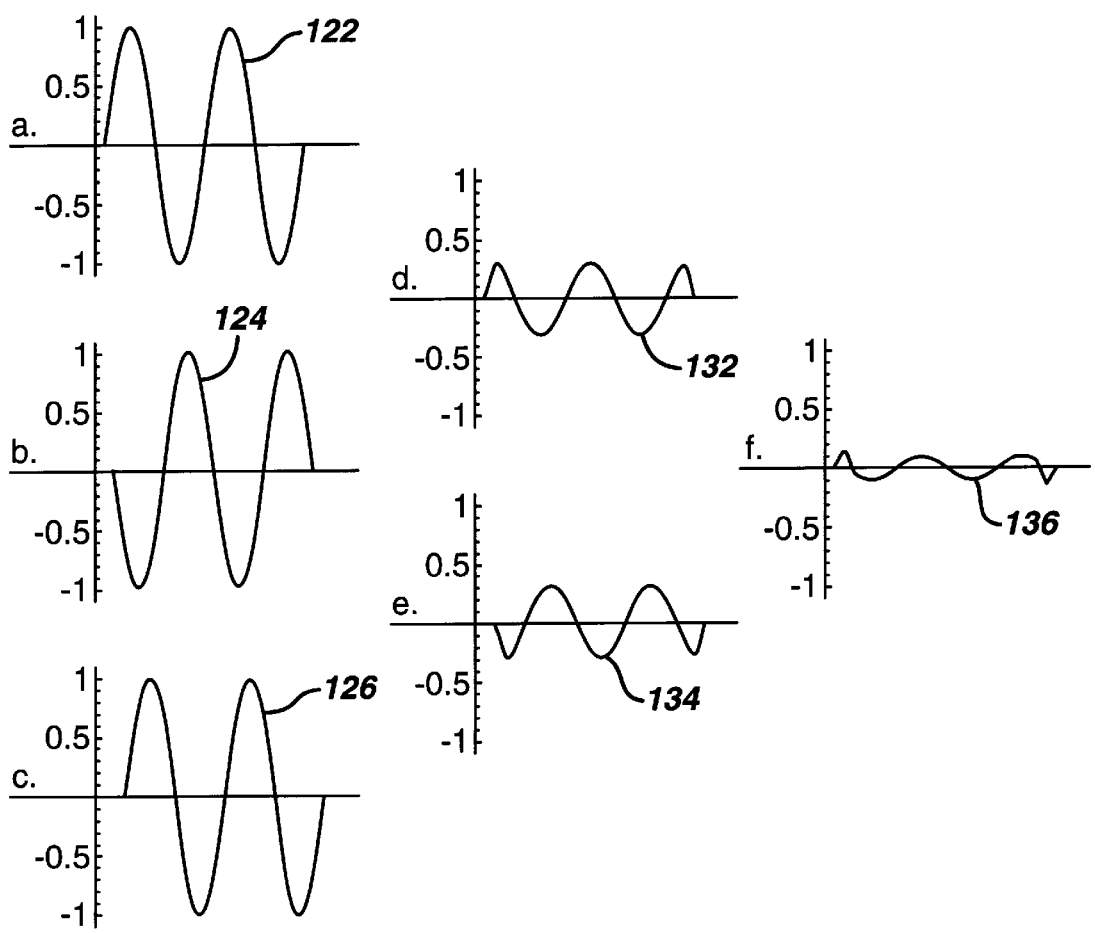
FIGS. 5a–5f illustrate echo waveforms depicting the operation of the embodiment of FIG. 4.

The reason for this improved fundamental cancellation in the presence of motion may be understood by referring to the drawings of FIG. 5. FIG. 5a, b, and c illustrate three fundamental frequency echo waveforms 122, 124, and 126 received from a moving object in response to alternate polarity transmit pulses. As these three drawings show, the three waveforms are all of the same normalized amplitude of one, and are progressively shifted in time from one to the next due to the motion of the object. When waveforms 122 and 124 are combined the partial sum signal 132 of FIG. 5d results, and when waveforms 124 and 126 are combined the partial sum signal 134 of FIG. 5e results. As these drawings illustrate, about 70% of the fundamental signal is cancelled in each case. The degree of fundamental cancellation is a function of the velocity with which the object is moving and hence the time shift between the combined waveforms; in the limit, when the object has a velocity of zero (is not moving) there is 100% complete cancellation of the fundamental component. The degree of cancellation is about 70% in this example in both of the partial sum signals 132 and 134 because the time intervals between the transmit pulses are uniform and the velocity is approximately constant over the three pulse interval, a reasonable assumption. When the partial sum signals 132 and 134 are combined, the function of adder 116 in FIG. 4, the final sum signal 136 of FIG. 5f results. In this signal the fundamental components are reduced by approximately another 60%, which reduces the fundamental component amplitude to approximately 12% of that of the original received echoes. The degree of fundamental cancellation in this final sum signal is maximized by maintaining equal time intervals between the transmit pulses so that the partial sum signals 132 and 134 exhibit approximately equal amplitudes and with therefore maximally cancel when combined.

For optimal cancellation the target should be within the beam sensitivity of all of the beams whose signals are being combined. This is readily achieved by aligning the beams so that they are identically steered or substantially overlapping from one beam to the next. The substantially overlapping beams outlined by beam patterns 102, 102' and 102" would be effective for harmonic separation of echoes produced by the target in FIG. 3a, for instance. Beams which are spatially distinct from each other lack the beam-to-beam correlation necessary for best cancellation as the signal content will be a function of different anatomical interrogations.

Even greater cancellation will be produced by using a fourth echo, producing two levels of partial sums before the final sum result. This extension is shown in the following sequence:

$$
\begin{aligned}
P1^+ &\to I_1^+ \\
+ & \\
P2^- &\to (I_1^+ + I_2^-) \\
+ & \quad + \\
P3^+ &\to (I_2^- + I_3^+) \to (I_1^+ + 2*I_2^- + I_3^+) \\
+ & \quad + \quad\quad + \\
P_4^- &\to (I_3^+ + I_4^-) \to (I_2^- + 2*I_3^+ + I_4^-) \to (I_1^+ + 3*I_2^- + 3*I_3^+ + I_4^-) \\
+ & \quad + \quad\quad + \quad\quad + \\
P5^+ &\to (I_4^- + I_5^+) \to (I_3^+ + 2*I_4^- + I_5^+) \to (I_2^- + 3*I_3^+ + 3I_4^- + I_5^+) \to (I_1^+ + 4*I_2^- + 6*I_3^+ + 4I_4^- + I_5^+) \\
\vdots & \quad \vdots \quad\quad \vdots \quad\quad \vdots \quad\quad \vdots
\end{aligned}
$$

The first three lines of the sequence illustrate the partial sums and final sum described above. When the echo $I_4^-$ from a fourth pulse P4$^-$ is acquired, another partial sum $(I_3^+ + I_4^-)$ is produced. This makes possible a second level partial sum of the form $(I_2^- + 2I_3^+ + I_4^-)$ which, when combined with the previous partial sum of the same level (and the final result of the three pulse example above), yields a four pulse result of the form $(I_1^+ + 3I_2^- + 3I_3^+ + I_4^-)$ with even greater fundamental component cancellation than that of the three pulse result.

Figure 6:
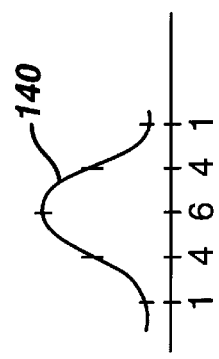
FIG. 6 illustrates approximate Gaussian varying coefficients for a filter structure embodiment of the present invention.

The series of coefficients of each final sum on the right-hand side of the above sequence are seen to vary in an approximate Gaussian manner in each case, beginning with a small value, then rising to a maximum value, then declining to a small value. The four pulse sum has the illustrated coefficients of 1-3-3-1, and the five pulse sum is seen to have the coefficient series of 1-4-6-4-1. These coefficient sequences may be conveniently calculated by what is known as the rule of Pascal's triangle. This rule is expressed mathematically as $(a+b)^{(n-1)}$ where n is the number of echo signals being combined for harmonic separation. For example, when three echo signals are being combined, n=3 and $(a+b)^{(3-1)} = a^2 + 2ab + b^2$ which has coefficients of 1, 2, and 1. When four echo signals are being combined, n=4 and $(a+b)^{(4-1)} = a^3 + 3a^2b + 3ab^2 + b^3$, the coefficient series described above. For five echoes the rule of Pascal's triangle produces the coefficient series of 1-4-6-4-1. As FIG. 6 illustrates, the coefficient series of the rule of Pascal's triangle each exhibit approximately a Gaussian variation as indicated by the Gaussian curve 140. When it is desired that the separated harmonic signals also include a degree of fundamental signal components, which would be useful when both harmonic and fundamental components are being used to form an image, an example of which is shown in U.S. Pat. No. 5,908,389, the fundamental component cancellation can be intentionally degraded by altering the coefficients from those produced by the rule of Pascal's triangle.

Figure 7:
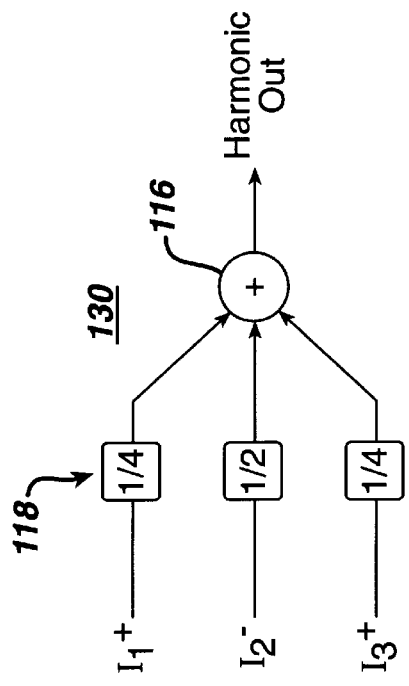
FIG. 7 illustrates a normalized three tap filter structure embodiment of the present invention.

In accordance with a further aspect of the present invention, pulse inversion harmonic separation may be performed by a filter structure using the foregoing coefficient series which is equivalent to the above description. Preferably the coefficients are scaled so that they sum to unity, enabling the filter structure to normalize the output signal as it performs harmonic separation. FIG. 7 illustrates a filter structure 130 for a three echo sequence $I_1^+$, $I_2^-$, and $I_3^+$. The Pascal's triangle coefficients of 1-2-1 for three echoes is scaled to add to one, yielding coefficients of ¼, ½, and ¼. These scaled coefficients are applied by weighting circuits 118 which may comprise multipliers of the filter structure 130, and the three weighted signals are combined by a summer 116 to produce separated and normalized harmonic signals with reduced fundamental components.

Figure 8B:
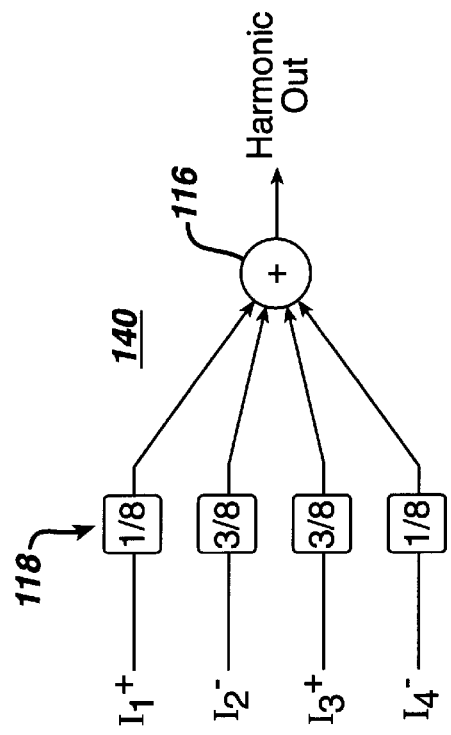
FIGS. 8a and 8b illustrate a filter structure which performs normalized pulse inversion harmonic separation with reduced motional effects using weighting coefficients established by the rule of Pascal's triangle.
Figure 8A:
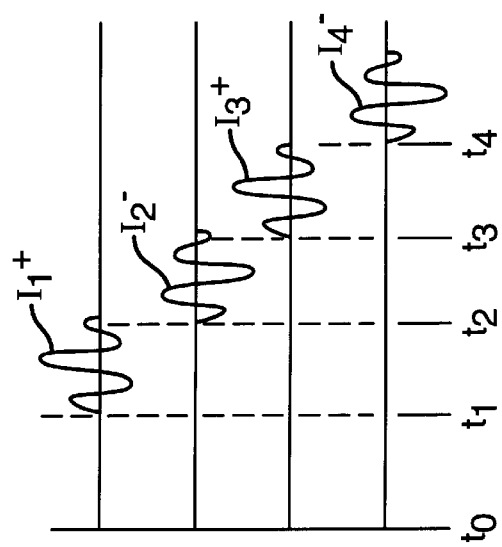

FIGS. 8a and 8b illustrate extension of the filter structure embodiment to four echoes. The illustrated echoes $I_1^+$, $I_2^-$, $I_3^+$ and $I_4^-$ are acquired at equally separated points in time $t_1$, $t_2$, $t_3$, and $t_4$ in response to transmit pulses of alternating phase or polarity. With the echoes separated by equal time intervals, the alternating polarity echoes are applied to the inputs of filter structure 140 where they are weighted by weighting coefficients ⅛, ⅜, ⅜, and ⅛ and summed by adder 116 to produce separated and normalized harmonic signals from a four pulse sequence.

Besides Gaussian distributions, coefficient series having other variations may be used to cause different degrees of fundamental suppression during harmonic separation. For example, the coefficients of the series may start at a low value and progress to a high value, or the coefficients may start at a high value and progress to a low one.

When the echo signals are not uniformly spaced in time, a filter structure can still be used, preferably by adjusting the weighting coefficients of weighting circuits 118 in relation to the time spacings of the echoes.

Figure 9:
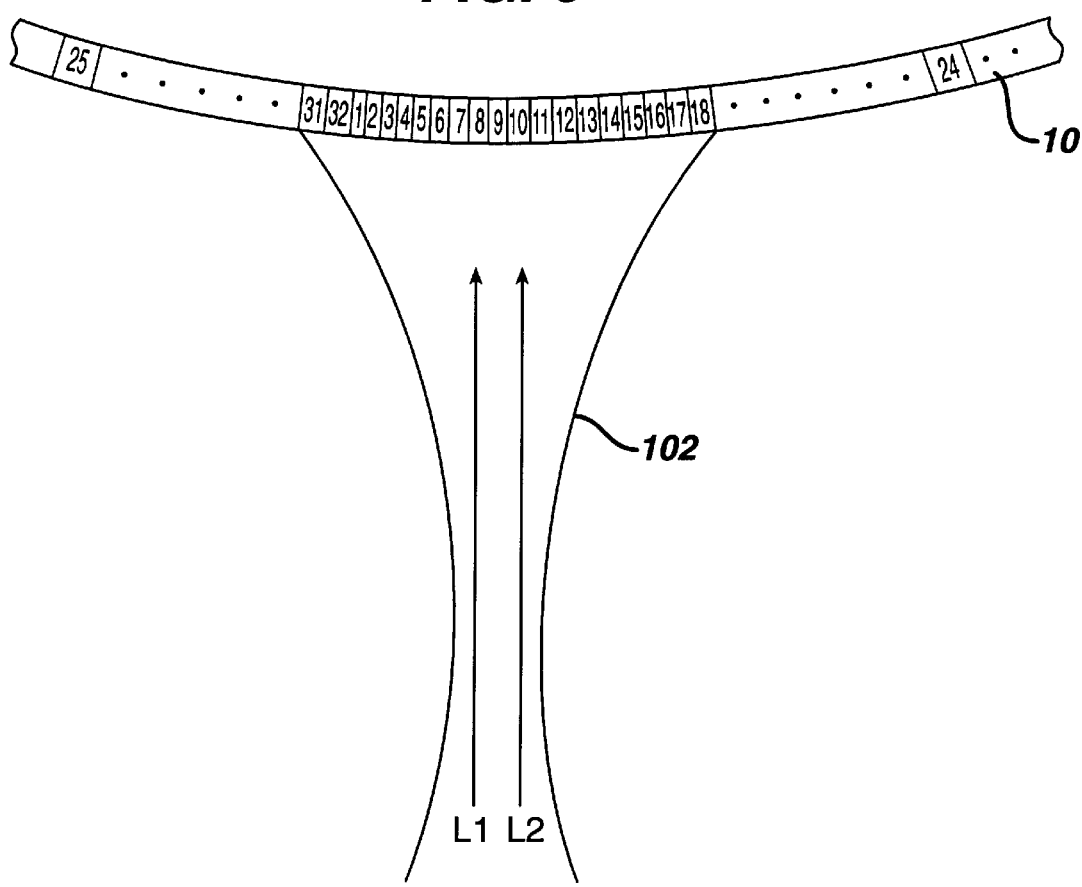
FIG. 9 illustrates the production of multiline signals for harmonic separation in accordance with the principles of the present invention.

For high frame rate operation echoes from adjacent scanlines can be acquired simultaneously using a conventional multiline beamformer. Referring to FIG. 9, the beam profile 102 is wide enough so that two scanlines L1 and L2 are insonified simultaneously by the same transmit beam. Transmit beams of opposite phase or polarity are alternately transmitted to simultaneously insonify the two scanlines L1 and L2, and echoes are simultaneously formed for the two scanlines by using two sets of steering delays in the beamformer. The first beam transmission results in an $I_1^+$ echo for each scanline, the second beam transmission results in an $I_2^-$ echo for each scanline, and so forth until the complete set of echoes for pulse inversion is acquired for each scanline. The sequences of echoes are combined as shown in FIG. 4 or weighted and combined as shown in FIGS. 7 and 8a by two processors or filter structures to produce two lines of separated harmonic signals simultaneously, or by one processor or filter structure in time alternating succession. With additional delays the received echo signals can be processed to simultaneously form three, four, or more scanlines simultaneously for pulse inversion harmonic separation.

Figure 10:
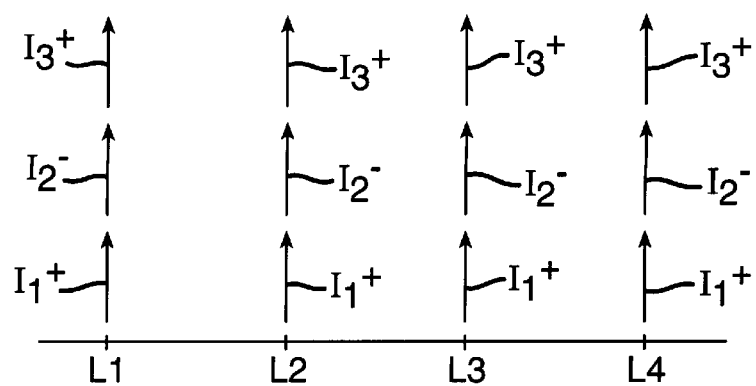
FIG. 10 illustrates time interleaved acquisition of alternate polarity echoes for harmonic separation in accordance with the present invention.

The echo sequences for an embodiment of the present invention may be acquired in a time interleaved manner if desired. This may be desirable when a low PRF (pulse repetition frequency) is desired for low velocity flow diagnosis, for instance. FIG. 10 illustrates four spatially adjacent lines L1, L2, L3, and L4. In this example each line of harmonic signals is to be produced by pulse inversion separation using a three pulse sequence. The echoes for each line could be acquired in a group of $I_1^+$, $I_2^-$, and $I_3^+$ as described above. However, the sequences for the four lines could also be acquired in a time interleaved manner. For instance, a pulse of one phase or polarity is transmitted on each line to acquire an $I_1^+$ sequence of echoes for each of lines L1, L2, L3 and L4. Then a pulse of the opposite phase or polarity is transmitted on each line to acquire an $I_2^-$ sequence of echoes for each line. Finally, for a three pulse sequence, a pulse of the first phase or polarity is transmitted on each line to acquire an $I_3^+$ sequence of echoes for each line. The echoes of each line are then combine or weighted and summed as described above to produce separated harmonic signals for four ultrasonic image lines. Various combinations of interleaving are also possible. In addition to the [++++,----,++++] pulse sequence just described in FIG. 10, sequences such as [+-+-,-+-+,+-+-] and [++--,--++,++--] may be employed in consideration of desired PRF and data processing characteristics of a particular diagnostic application or ultrasound system.

Figure 11:
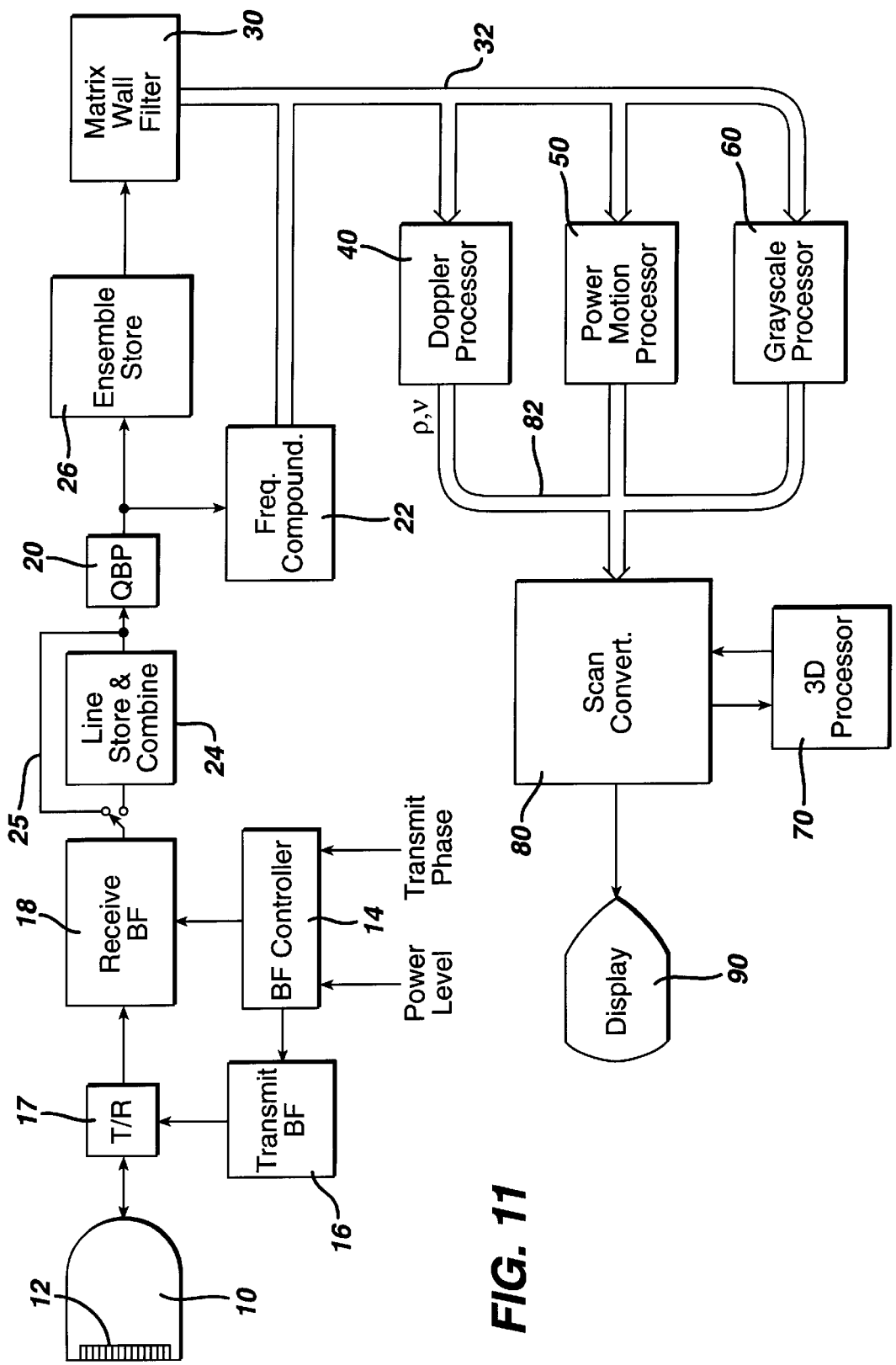
FIG. 11 illustrates in block diagram form an ultrasonic diagnostic imaging system which performs Doppler, power motion, and grayscale harmonic imaging in accordance with the principles of the present invention.

FIG. 11 illustrates in block diagram form an ultrasonic diagnostic imaging system for performing pulse inversion harmonic separation in accordance with the principles of the present invention. A probe 10 which includes an array transducer 12 transmits ultrasonic energy into the body and receives echoes returned from tissue, cells and flowing substances in the body, including moving tissue and/or ultrasonic contrast agents. The array transducer can be a linear or curved array, and can be operated as a phased array or linear array. Phased array operation is often preferred for cardiology applications. The timing of transmission and reception by the array transducer is synchronized by a beamformer controller 14 which is connected to a transmit beamformer 16 and a receive beamformer 18. The channels of each beamformer are connected to the individual elements of the array transducer so as to separately control the transmission and reception of signals from the individual elements. The transmit beamformer 16, under control of the beamformer controller, determines the time at which each element in the array is actuated to transmit a wave or pulse. This controlled timing of transmission enables the transmit beam 102 to be steered in a given direction, that is, along a predetermined scanline, and to be focused at the desired depth of focus. The beamformer controller 14 is also responsive to a Power Level control signal set by the user which sets the power level of the transmit energy, and is responsive to a Transmit Phase control signal which controls the relative phase or polarity of the transmit pulses. The channels of the two beamformers are coupled to elements of the array by transmit/receive switches 17 which protect the receive beamformer channel inputs from high transmit voltages.

The echoes received by individual transducer elements are coupled to individual channels of the receive beamformer 18 by the transmit/receive switches 17. These input paths may also include preamplifiers to amplify the received echo signals and time gain compensation circuits to compensate for the effects of depth dependent attenuation. When the receive beamformer 18 is a digital beamformer as it is in the preferred embodiment, each channel of the beamformer is preceded by or includes an analog to digital converter. The channels of the beamformer continuously appropriately delay the echoes received by each transducer element from along the scanline so that the signals received from common points (sample volumes) along the scanline are brought into time coincidence. The continual delay variation effects dynamic focusing of the received echo signals along the scanline. The signals at the outputs of the channels are then combined to form a sequence (scanline) of coherent echo signals.

Receive beamformers also conventionally perform other processing operations such as normalization of signal amplitudes to offset the effects of dynamic aperture changes. The receive beamformer may also be partitioned into two or more groups of channels, each with its own unique delay programming from the beamformer controller, to perform multiline reception. In multiline reception, each group of channels steers and focuses a received beam along its own scanline, thereby forming two or more received scanlines simultaneously.

In one mode of operation, the sequence of coherent echoes received along the scanline are pulse inversion processed, detected, scaled to a range of grayscale values, scan converted to the desired image format, and displayed, thus forming a B mode image. In the apparatus of FIG. 1, the coherent echoes produced by the beamformer 18 are coupled to a line store & combining circuit 24 which performs harmonic separation by the pulse inversion technique described above. Each sequence of echoes received following a transmit pulse is stored in the line store & combining circuit until all of the signals which are to be combined for harmonic separation have been received. The sequences of echoes are then processed by the combining portion of the line store & combining circuit which may take the form shown in any of FIGS. 4, 7 or 8b. The separated harmonic signals are demodulated by a quadrature bandpass (QBP) filter 20 into in-phase (I) and quadrature (Q) harmonic samples in a predetermined passband. The passband defined by the QBP filter can also roll off any residual fundamental frequency components and unwanted out-of-band signals. For harmonic imaging the passband is located at a band of harmonic frequencies of the fundamental transmit frequency. The I,Q samples can be Doppler processed to determine Doppler power, velocity, acceleration, variance, and the direction of flow or motion, and can also be used to detect the amplitude of the echo signal by the algorithm $(I^2+Q^2)^{1/2}$. For B mode imaging the I,Q samples are processed to remove speckle by frequency compounding circuit 22. The samples are then applied to a grayscale processor 60 by way of an echo data bus 32, where the echoes undergo detection, log compression and grayscale mapping. The grayscale signals are coupled to a scan converter 80 by way of an image data bus 82, where the R-θ scanline data is converted to the desired display format. The grayscale signals may be processed for 3D display by a 3D processor 70. The scan converted image is displayed on a display 90.

A power motion processor 50 is provided for the power motion imaging mode. The power motion processor can receive two or more temporally different harmonic echoes from a sample volume and differentiates the signals on an amplitude basis. The differential result is indicative of motion, is scaled to a range of display values and displayed, preferably in color in combination with a B mode structural image. Power motion imaging is described in further detail in U.S. Pat. No. 5,718,229. In an embodiment of the present invention, the result is that echo samples used to separate harmonic components from fundamental components are separated in a manner which reduces motional effects among the echoes used to separate a harmonic signal. Different harmonic signals developed in this way from the same sample volume but at different time periods will continue to exhibit motional effects from one harmonic signal to another. The temporal difference between these time periods sets the PRI or pulse repetition interval of the harmonic signals. The power motion processor takes advantage of this fact to image motion, as does the Doppler processor described below.

For Doppler imaging a scanline is repetitively scanned over an interval of time to gather a sequence of temporally distinct echoes at each sample volume along the scanline. This temporal echo sequence, called an ensemble, is acquired by a sequence of transmit pulses, the repetition frequency of which is called the pulse repetition frequency, or PRF. Each individually transmitted wave or pulse exhibits a nominal frequency which is in the normal r.f. range of diagnostic ultrasound. PRFs are usually in the kilohertz range or lower. For Doppler processing the line store & combining circuit 24 is bypassed as indicated by signal path 25. The echo ensembles are quadrature demodulated by the QBP filter and accumulated in an ensemble store 26 from which completed ensembles are produced for Doppler processing.

The conventional first step in Doppler processing is wall filtering. When imaging or measuring bloodflow in the heart and blood vessels, the relatively low level echoes from blood cells can be overwhelmed by strong echoes reflected by nearby tissue such as a vessel or heart wall. Since the intent of the procedure is to image or measure bloodflow, the tissue echoes are, in this instance, clutter which can be eliminated. The circuitry which eliminates these unwanted signals is called a wall filter, since its basic purpose is to eliminate echoes from the heart and vessel walls. These signals may be discriminated by amplitude, frequency, or a combination of these two characteristics since tissue signals are generally of greater amplitude and lower Doppler frequency than bloodflow signals. A preferred technique for eliminating tissue signals as well as Doppler motion artifacts known as "flash" is shown in U.S. Pat. No. 5,197,477.

The wall filter may also be operated with a reverse characteristic so as to pass tissue Doppler signals to the exclusion of bloodflow Doppler signals. When these signals of the tissue are Doppler processed, images of moving tissue such as the heart muscle and valves can be produced. This imaging technique is known as tissue Doppler imaging. The tissue Doppler signals can also be applied to the power motion processor 50 where they can be used for power motion imaging.

In the embodiment of FIG. 11, the wall filter 30 also performs harmonic separation for Doppler signals. The matrix used by the matrix wall filter includes coefficient values developed as described above to separate harmonic components from received echoes of differing polarity transmit signals. As the wall filter processes these alternating polarity echoes, it simultaneously performs harmonic separation by pulse inversion and imposes a filter characteristic on the resultant harmonic signals which can reject stationary or slowly moving tissue as well as residual fundamental components. For tissue Doppler imaging the wall filter characteristic can reject stationary tissue and bloodflow signals or only bloodflow signals, as well as the fundamental frequency band. Filter characteristics of sharper cutoff or of a tailored nonlinearity can be provided by using a greater number of samples in the wall filter (i.e., a longer filter). Thus, an ensemble of harmonic echoes are produced at each sample volume location in which individual harmonic signals are produced by suppression of motional effects which degrade harmonic separation, with the samples of the ensemble still retaining the phase shift characteristics of the desired harmonic signal to harmonic signal motion.

The filtered Doppler signals, bloodflow or tissue, are applied to a Doppler processor 40 where they are used to perform Doppler estimation of the Doppler phase shift (velocity v) or signal intensity (power Doppler p) as described in U.S. patent [application Ser. No. 09/079,139]. Conventionally this is done by a Fourier transformation or autocorrelation of the Doppler signal data. A preferred technique is to perform a two dimensional autocorrelation which simultaneously estimates the Doppler phase shift and the reference or center frequency of the Doppler signal. The latter is useful for correction of the effects of depth dependent frequency attenuation in the phase shift estimation. Such a two dimensional Doppler processor is described in U.S. Pat. No. 5,386,830. Since the Doppler frequency or phase shift is proportional to the velocity of the bloodflow or tissue which returned the echoes, the production of a velocity, acceleration or variance estimate is straightforward. In colorflow Doppler the velocities of bloodflow are mapped to a color scale, coupled to the scan converter 80 over the image data bus 82, and overlaid on a grayscale image of the tissue structure containing the bloodflow. In power Doppler imaging the intensity of the Doppler signals is similarly mapped and displayed on a grayscale image. Doppler and grayscale image data can also be processed by 3D processor 70 to form three dimensional image presentations of the bloodflow and/or tissue, as described in U.S. Pat. Nos. 5,474,073 and 5,720,291.

What is claimed is:

1. A method for separating fundamental and harmonic components of an ultrasonic echo signal comprising the steps of:

interrogating a sample volume with a sequence of four or more fundamental frequency transmit pulses of two differing phases or polarities;

receiving a sequence of four or more temporally differing echoes of differing phases or polarities in response to said transmit pulses; and combining one set of pairs of echoes of differing phase or polarity to form a first partial sum of pairs of echoes;

combining another set of pairs of echoes of differing phase or polarity to form a second partial sum of pairs of echoes; and utilizing said partial sums in a weighted combination to form separated harmonic signal components with reduced motional effects.

2. The method of claim 1, wherein said step of utilizing comprises the step of combining said partial sums.

3. The method of claim 1, further comprising the step of:

combining said two partial sums to form at least one second level partial sum; and wherein said step of utilizing utilizes said second level partial sum to form separated harmonic signal components with reduced motional effects.

4. The method of claim 3, further comprising the step of:

combining a third set of pairs of echoes of differing phase or polarity to form a third partial sum of pairs of echoes;

combining said second and third partial sums to form another second level partial sum; and wherein said step of utilizing combines said second level partial sums to form separated harmonic signal components with reduced motional effects.

5. The method of claim 1, wherein said pairs of echoes are of the form $(I_1^+ + I_2^-)$, $(I_2^- + I_3^+)$ and $(I_3^+ + I_4^-)$; and wherein said partial sums are of the form $(I_1^+ + 2I_2^- + I_3^+)$ and $(I_2^- + 2I_3^+ + I_4^-)$.

6. An ultrasonic diagnostic harmonic imaging system comprising:

a transmitter which transmits fundamental frequency transmit pulses of two different phases or polarities to a substance in the body which may be moving;

a receiver which receives temporally discrete echoes of different phases or polarities from said substance in response to said transmit pulses;

a filter structure having inputs to which four or more of said temporally discrete echoes are applied, weighting coefficients for weighting said echoes, and a summer at which harmonic signals with reduced fundamental components are produced, wherein said weighting coefficients for a series of alternate phase or polarity echoes exhibit a sequence which increases from a low value to a high value, and decreases to a low value.

7. The ultrasonic diagnostic harmonic imaging system of claim 6, wherein said sequence of weighting coefficients exhibit approximately a Gaussian distribution.

8. The ultrasonic diagnostic harmonic imaging system of claim 6, wherein said weighting coefficients are approximately equal to those calculated by the rule of Pascal's triangle.

9. The ultrasonic diagnostic harmonic imaging system of claim 6, wherein said sequence of weighting coefficients are approximately equal to coefficients calculated by the expression $(a+b)^{(n-1)}$ where n is the number of non-zero weighted echoes summed by said summer.

10. The ultrasonic diagnostic harmonic imaging system of claim 6 or 8, wherein said weighting coefficients are normalized to a nominal value.

11. The ultrasonic diagnostic harmonic imaging system of claim 10, wherein said nominal value is unity.

12. The ultrasonic diagnostic imaging system of claim 6, wherein said filter structure comprises:

a plurality of input taps to which received echoes are applied;

a plurality of weighting circuits which weight said received echoes; and a summer which sums weighted echo signals.

13. The ultrasonic diagnostic imaging system of claim 6 or 8, wherein said filter structure comprises a Doppler signal processor.

14. The ultrasonic diagnostic imaging system of claim 13, wherein said Doppler signal processor further comprises a wall filter.

15. The ultrasonic diagnostic imaging system of claim 6, wherein said filter structure comprises a B mode signal processor.

16. The ultrasonic diagnostic imaging system of claim 6 or 8, wherein said transmitter transmits pulses to two or more laterally discrete locations and said receiver receives echoes from said laterally discrete locations in a time interleaved manner.

17. The ultrasonic diagnostic imaging system of claim 16, wherein said time interleaving affects the PRI for echoes received from a given location.

18. The ultrasonic diagnostic imaging system of claim 6 or 8, wherein said transmitter transmits pulses to simultaneously insonify two or more laterally discrete locations and wherein said receiver comprises a multiline receiver which forms echoes from said laterally discrete locations following a transmit pulse.

19. The ultrasonic diagnostic imaging system of claim 6 or 8, wherein said substance comprises a harmonic contrast agent.

20. The ultrasonic diagnostic imaging system of claim 6 or 8, wherein said substance comprises moving tissue.

21. A method for separating harmonic components of an ultrasonic echo signal comprising the steps of:

transmitting fundamental frequency transmit pulses of two different phases or polarities to a target location in the body which may be moving;

receiving temporally discrete echoes of different phases or polarities from said target location in response to said transmit pulses;

separating harmonic components of said echoes with a filter structure having inputs to which four or more of said temporally discrete echoes are applied, weighting coefficients for weighting said echoes, and a summer, wherein said weighting coefficients exhibit a sequence which increases from a low value to a high value and decreases to a low value so as to reduce motional effects in said separated components.

22. The method of claim 21, wherein said filter structure further performs the step of normalizing the separated harmonic components to a nominal reference level.

23. The method of claim 21, wherein said weighting coefficients exhibit approximately a Gaussian variation.

24. The method of claim 21, wherein said weighting coefficients exhibit a variation which substantially follows the rule of Pascal's triangle.

25. The method of claim 24, wherein said weighting coefficients are offset from the rule of Pascal's triangle by an amount which imparts a desired fundamental content to separated harmonic components.

26. The method of claim 21, wherein said step of transmitting comprises the step of:

transmitting pulses to two or more laterally discrete locations in a time interleaved manner.

27. The method of claim 26, wherein said manner of time interleaving affects the PRI for echoes received from a given location.

28. The method of claim 21, wherein said step of transmitting comprises the step of simultaneously insonifying two or more laterally discrete locations; and wherein said step of receiving comprises the step of receiving echoes from two or more laterally discrete locations in response to a single pulse transmission.

29. An ultrasonic diagnostic harmonic imaging system comprising:

a transmitter which transmits fundamental frequency transmit pulses of two different phases or polarities to a substance in the body which may be moving;

a receiver which receives temporally discrete echoes of different phases or polarities from said substance in response to said transmit pulses;

a filter structure having inputs to which four or more of said temporally discrete echoes are applied, weighting coefficients for weighting said echoes, and a summer at which harmonic signals with reduced fundamental components are produced,
wherein said weighting coefficients for a series of alternate phase or polarity echoes exhibit a sequence which increases from a low value to a high value.

30. An ultrasonic diagnostic harmonic imaging system comprising:

a transmitter which transmits fundamental frequency transmit pulses of two different phases or polarities to a substance in the body which may be moving;

a receiver which receives temporally discrete echoes of different phases or polarities from said substance in response to said transmit pulses;

a filter structure having inputs to which four three or more of said temporally discrete echoes are applied, weighting coefficients for weighting said echoes, and a summer at which harmonic signals with reduced fundamental components are produced,
wherein said weighting coefficients for a series of alternate phase or polarity echoes exhibit a sequence which decreases from a high value to a low value.

* * * * *